United States Patent
Upadhyay et al.

(10) Patent No.: US 7,368,529 B2
(45) Date of Patent: May 6, 2008

(54) AGENT AND COMPOSITIONS COMPRISING THE SAME FOR INHIBITING LIPASES AND PHOSPHOLIPASES IN BODY FLUIDS, CELLS AND TISSUES

(75) Inventors: Shakti N. Upadhyay, Nerul Navi Mumbai (IN); Raman P. Yadav, Nerul Navi Mumbai (IN); Arif Ansari, Bombay (IN); Harinarayana Rao, Navi Mumbai (IN)

(73) Assignee: Reliance Life Science Pvt. Ltd., Maharashtra (IN)

( * ) Notice: Subject to any disclaimer, the term of this patent is extended or adjusted under 35 U.S.C. 154(b) by 0 days.

(21) Appl. No.: 11/093,637

(22) Filed: Mar. 30, 2005

(65) Prior Publication Data

US 2006/0147439 A1 Jul. 6, 2006

Related U.S. Application Data

(60) Provisional application No. 60/557,624, filed on Mar. 30, 2004.

(51) Int. Cl.
- *A61K 38/00* (2006.01)
- *C07K 5/00* (2006.01)
- *C07K 7/00* (2006.01)
- *C07K 16/00* (2006.01)
- *C07K 17/00* (2006.01)

(52) U.S. Cl. .......................................... 530/324; 514/2
(58) Field of Classification Search .................... 514/2
See application file for complete search history.

*Primary Examiner*—Cecilia J. Tsang
*Assistant Examiner*—Maury Audet
(74) *Attorney, Agent, or Firm*—J. Harold Nissen; Lackenbach Siegel, LLP

(57) ABSTRACT

The present invention deals with a protein and compositions comprising the same for inhibition of lipases and phospholipases in the body fluids, cells, and tissues for the prevention and treatment of metabolic syndrome, cardiovascular disorders, and inflammatory diseases. The protein is either isolated from plant species or synthesized or produced by recombinant DNA technology.

1 Claim, No Drawings

AGENT AND COMPOSITIONS COMPRISING THE SAME FOR INHIBITING LIPASES AND PHOSPHOLIPASES IN BODY FLUIDS, CELLS AND TISSUES (This invention claims priority from Provisional U.S. patent Application with Ser. No. 60/557,624 filed on 30th Mar. 2004)

1. FIELD OF THE INVENTION

The present invention relates to a protein and composition comprising the protein for inhibiting or reducing lipases and phospholipase enzymes in body fluids, cells, and tissues. The protein as described in the present invention and the composition comprising of the same are useful for the prevention or treatment of clinical manifestations and diseases caused as a consequence of lipase and phospholipase enzyme activities in the body fluids, cells, and tissues.

2. DESCRIPTION OF THE PRIOR ART

Lipases and phospholipases are key control elements in mammalian metabolism. They share many common features that set them apart from other metabolic enzyme classes, most importantly their association with "two-dimensional" substrates, i.e., lipid droplets, lipoproteins, phospholipid layers, biomembranes, and the resulting implications for their cleavage mechanism and regulation.

The pancreatic lipase (PL) is believed to be effective in causing a partial hydrolysis of triglycerides to obtain fatty acids and monoglycerides that, together with the bile acids, form complexes, which are then absorbed through the intestinal mucosa. Hepatic lipase (HL) and lipoprotein lipase (LPL) are the two major lipolytic enzymes responsible for the hydrolysis of triglycerides and phospholipids present in circulating plasma lipoproteins. Both lipases are attached to the vascular endothelium via cell surface proteoglycans. HL is primarily involved in the metabolism of chylomicron remnants, intermediate density lipoproteins, and high-density lipoproteins, whereas LPL catalyzes the hydrolysis of triglycerides from chylomicrons and very low-density lipoproteins. In addition to their traditional function as lipolytic enzymes, HL and LPL appear to serve as ligands that mediate the interaction of lipoproteins to cell surface receptors and/or proteoglycans.

Accumulation and distribution of triglyceride-rich lipoprotein-associated fatty acids at extra-hepatic sites is facilitated by LPL. The enzyme is also involved in several non-lipolysis associated functions, including the cellular uptake of whole lipoprotein particles and lipophilic vitamins. The tissue-specific variations of LPL expression have been implicated in the pathogenesis of various lipid disorders, obesity, and atherosclerosis. LPL expressed by cells of the vascular wall, particularly macrophages, have identified additional actions of the enzyme that contribute to the promotion of foam cell formation and atherosclerosis. Development of drugs specifically acting on the cholesteryl ester transfer protein and lipoprotein lipase systems, are being explored.

Over the past several years significant advances have been made in our understanding of new, alternative mechanisms by which HL and LPL modulate lipoprotein metabolism and the development of atherosclerosis in vivo. Advances have also been made in our understanding of the intravascular metabolism of triglyceride-rich lipoproteins. It is now known that the complex extracellular interactions of triglyceride-rich lipoprotein-associated apolipoprotein E, lipoprotein lipase, and hepatic lipase with heparan sulfate proteoglycans and lipoprotein receptors facilitate the hepatocellular uptake of triglyceride-rich lipoproteins. Recent studies have also revealed that the intracellular fate of internalized triglyceride-rich lipoproteins is highly complex. The dissociation of triglyceride-rich lipoprotein components within intracellular endosomal compartments involves the recycling of apolipoprotein E, whereas the remaining lipid core associated with apolipoprotein B is susceptible to lysosomal degradation.

The high incidence of atherosclerosis in diabetic patients has been correlated with LPL activity in macrophages. Accumulating evidence indicates that LPL produced by macrophages in the vascular wall may favor the development of atherosclerosis by promoting lipid accumulation within the lesion.

The potential of lipases as drug targets for the treatment of metabolic syndrome and cardiovascular disorders is increasingly recognized. It is now believed that the front line therapy for diseases related to lipid absorption and metabolism should be to inhibit or reduce lipase activity in the body fluids, cells, and tissues.

Lipase inhibitors have been reported from various natural products, especially from microbial sources. The example of such inhibitors include lipstatin and Panclicins A-E from *Streptomyces* species or their synthetic derivatives that inhibit the hydrolysis of triglycerides and cholesterol esters (Hochuli et al., *Lipstatin, and Inhibitor of Pancreatic Lipase, Produced by Streptomyces Toxytricini, II. Chemistry and Structure Elucidation*, J. Antibiot. (Tokyo), 1987 Aug., 40(8):1086-91; Fernandez et al., *Effects of Tetrahydrolipstatin, a Lipase Inhibitor, on Absorption of Fat from the Intestine of the Rat*, Biochim. Biophys. Acta., 1989 Feb. 20, 1001(3):249-55; Yoshinari et al, *Panclicins, Novel Pancreatic Lipase Inhibitors, II. Structural elucidation*, J. Antibiot. (Tokyo), 1994 Dec., 47(12):1376-84) and is being used for treatment of obesity (U.S. Pat. No. 5,540,917). Besides, a number of molecules have been identified from plant sources including tannins isolated from *Cassia nomame* (U.S. Pat. No. 5,629,338). LPL has been shown to be involved in the pathogenesis of atherosclerosis (Mead et al, *Lipoprotein Lipase, a Key Role in Atherosclerosis?*, FEBS Lett., 1999 Nov. 26, 462(1-2):1-6). Inhibition of LPL is believed to prevent the atherosclerotic process (Zimmerman et al., *Lipoprotein Lipase Mediates the Uptake of Glycated LDL in Fibroblasts, Endothelial Cells, and Macrophages*, Diabetes, 50, 1643-1653, 2001).

Phospholipases specifically act on and hydrolyse membrane phospholipids and generate mediators implicated in signal transduction and inflammatory processes. The role of phospholipase A2 (PLA2) is well known in the generation of arachidonic acid, which is responsible for leukotriene and prostaglandin synthesis; PLA2 inhibitors have been proposed as drugs for variety of inflammatory and degenerative diseases. Lipoprotein-associated phospholipase A2 has been shown to be involved in atherosclerosis and its inhibition is being proposed for its treatment (Leach et al., *Lipoprotein-Associated PLA2 Inhibition—A Novel, Non-Lipid Lowering Strategy for Atherosclerosis Therapy*, Farmaco, 2001 January-February, 56(1-2):45-50).

3. SUMMARY OF THE INVENTION

The present invention relates to a protein and composition comprising the same for inhibiting or reducing lipases and phospholipase enzymes in body fluids, cells, and tissues.

The protein as described in the present invention and the composition comprising of the same are useful for the prevention or treatment of clinical manifestations and diseases caused as a consequence of lipase and phospholipase enzyme activities in the body fluids, cells, and tissues.

In the preferred embodiments the protein having lipase inhibitory activity can be synthesized, produced by recombinant technology or isolated from natural sources.

In the most preferred embodiments the protein is isolated from the seeds of plant species belonging to *Moringa* genus.

In the preferred embodiments the compositions for inhibition of lipases or phospholipases comprises of protein as described in the present invention in a therapeutically effective amount and pharmaceutically inert adjuvants, diluents or carriers.

In the preferred embodiments the compositions for inhibition of lipases or phospholipases comprising of protein as described in the present invention may also be combined with other active ingredients.

The protein as described in the present invention or composition comprising the same is believed to have the ability to inhibit lipases and phospholipases under physiological conditions, and thereby would have corresponding effectiveness for prevention or treatment of metabolic syndrome, cardiovascular disorders, and inflammatory diseases.

In the preferred embodiments the protein as described in the present invention or the compositions comprising proteins are useful as for inhibition of lipases and phospholipases in the body fluids, cells, and tissues for the prevention and treatment of metabolic syndrome, cardiovascular disorders, and inflammatory diseases.

In another embodiments, the protein as described in the present invention or the composition comprising a protein can be used for prevention or treatment of metabolic disorders like obesity, diabetes, and atherosclerosis.

In still another embodiments, the protein as described in the present invention or the composition comprising a protein can be used in inhibiting or reducing accumulation of lipids in monocytic cells, vascular cells, hepatocytes, and adipose tissues.

In yet another embodiments, the protein as described in the present invention or the composition comprising a protein can be used for prevention or treatment of inflammatory diseases, such as arthritis, atherosclerosis, and septic shock, that are caused by the activation and/or the action of phospholipases.

In yet another embodiments, the protein as described in the present invention or the composition comprising a protein can be used for skin and hair care and cosmetic preparations.

In yet another embodiments, the protein as described in the present invention or the composition comprising a protein can be used to prevent or treat cellular and tissue damage caused by microbial pathogens secreting lipases and phopholipases.

In yet another embodiments on basis of lipase inhibitory properties, the composition comprising a protein can be used in veterinary medicine for the treatment and prophylaxis of diseases caused or aggravated by lipase and phospholipase activity in the body fluids, cells and tissues.

In preferred embodiments the present invention also provides the pharmaceutical formulations comprising protein either alone or a suitable pharmceautically acceptable adjuvant useful in inhibition of lipases and phospholipases in the body fluids, cells, and tissues for the prevention and treatment of metabolic syndrome, cardiovascular disorders, and inflammatory diseases.

The present invention also provides the manner of manufacture of medicaments comprising of protein as described in the present invention in a therapeutically effective amount either alone or in combination with pharmaceutically acceptable adjuvant. The protein as described in the present invention may also be combined with other active ingredients.

4. DESCRIPTION OF THE INVENTION

The present invention relates to a protein containing 5-100 amino acid residues and having a molecular weight ranging from 0.5-10 kD, with or without glycosylation. The protein has inhibitory or reducing effect on lipase and phospholipase enzyme activities. The protein may be synthesized or produced through recombinant DNA technology or it may isolated from plant material.

The protein as disclosed in the present invention is isolated from species belonging to genus *Moringa*, more preferably it is isolated from seeds of plant *Moringa*. The protein can be isolated by the method as disclosed herein later under the examples.

The protein has partial sequence ID as following SEQ. ID. NO. 1

CGQQLRNISPPQRCPSLRQAVQLAHQQQGQGPQQVRQMYR

The present invention also relates to the compositions for inhibition of lipases or phospholipases comprising of protein as described in the present invention in a therapeutically effective amount and pharmaceutically inert adjuvants, diluents or carriers. The compositions for inhibition of lipases or phospholipases comprising of protein as described in the present invention may also be combined with other active ingredient or ingredients.

The protein as described in the present invention or composition comprising the same is believed to have the ability to inhibit lipases and phospholipases under physiological conditions, and thereby would have corresponding effectiveness for prevention or treatment of metabolic syndrome, cardiovascular disorders, and inflammatory diseases.

The protein as described in the present invention or the compositions comprising protein are useful for inhibition of lipases and phospholipases in the body fluids, cells, and tissues for the prevention and treatment of metabolic syndrome, cardiovascular disorders, and inflammatory diseases.

In the preferred embodiments the protein as described in the present invention or the composition comprising a protein can be used for prevention or treatment of metabolic disorders like obesity, diabetes, and atherosclerosis.

In further aspects the protein as described in the present invention or the composition comprising a protein can be used in inhibiting or reducing accumulation of lipids in monocytic cells, vascular cells, hepatocytes, and adipose tissues.

In still other aspects, the protein as described in the present invention or the composition comprising a protein can be used for prevention or treatment of inflammatory diseases, such as arthritis, atherosclerosis, and septic shock, that are caused by the activation and/or the action of phospholipases.

In still another aspects, the protein as described in the present invention or the composition comprising a protein can be used to prevent or treat cellular and tissue damage caused by microbial pathogens secreting lipases and phopholipases.

In yet another aspects, the protein as described in the present invention or the composition comprising a protein can be used for skin and hair care and cosmetic preparations.

The protein as described in the present invention or composition comprising the same can be administered in any conventional oral, buccal, nasal, by inhalation spray in unit dosage form, parenteral, (for example, intravenous, intramuscular, subcutaneous intrastemal or by infusion techniques), topical (for example, powder, ointment or drop), transdermal, intracisternal, intravaginal, intraperitoneal, intravesical, or rectal. In another aspect of the invention, the compound of the present invention and at least one other pharmaceutically active agent may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

The protein as described in the present invention or composition comprising the same can be administered in the form of any modified release, controlled release or timed release formulations.

Accordingly, formulations according to the present invention for reducing lipase and phospholipase activity in body fluids, cells, and tissues will comprise, as the essential active ingredient, the protein of the present invention.

In preferred embodiments the present invention provides formulations for reducing lipase and phospholipase activity in body fluids, cells, and tissues comprising the protein of the present invention, it ca be formulated either alone or in combination with a known pharmaceutically acceptable and inert adjuvant, diluent or carrier.

A formulation comprising the protein according to the present invention can be formulated together with one or more routine additives, carriers, assistants, and the like. It can be formulated for oral administration and can be used in the field of pharmaceuticals. Examples of suitable forms for oral administration include tablets, capsules, granules, fine granules, spherules, syrups, and drinks. In the preferred embodiments it is formulated in the form of spherules. In most preferred embodiments the spherules are enteric coated. Examples of suitable carrier materials are water, gelatin, gum arabic, lactose, starch, magnesium stearate, talc, vegetable oils, polyalkyleneglycols, petroleum jelly, etc. The pharmaceutical preparations can be made up in a solid form (e.g., as tablets, dragees, suppositories or capsules) or in a liquid form (e.g., as solutions, suspensions or emulsions). The pharmaceutical preparations may be sterilized and/or may contain adjuvants such as preservatives, stabilizers, wetting agents, emulsifiers, salts for varying the osmotic pressure, or buffers. They can also contain other therapeutically valuable substances.

For the preparation of a formulation according to the present invention, the essential ingredients are mixed with one or more pharmaceutically-acceptable vehicles, carriers, excipients, binders, antiseptics, anti-oxidants, stabilizers, taste corrigents, buffers, and the like, followed by formation into a desired unit dosage form.

Examples of adjuvants that can be incorporated in tablets, capsules, or the like, upon formulation according to the present invention include: binders such as gum arabic, corn starch, and gelatin; lubricants such as magnesium stearate; excipients, such as crystalline cellulose; swelling agents, such as gelatinized starch and arginic acid; sweeteners, such as sucrose, lactose, and saccharin; and taste corrigents, such as peppermint and cherry. Upon formulation into capsules, a liquid carrier, such as oil, can also be incorporated together with the above adjuvants.

Furthermore, other materials can be added as a coating agent or to change the physical form of the preparation. For example, tablets can be coated with shellac, sugar, or any acidic pH resistant polymer. Syrups and elixirs can be added with sucrose as a sweetener, methylparaben or propylparaben as an antiseptic, and/or peppermint or orange flavor as a taste corrigent.

According to the present invention, the formulation can be used as a medicament for lowering total serum lipid cholesterol, and for the treatment of obesity, ischemic heart diseases, arteriosclerosis, cerebrovascular dementia, diabetes, angiopathic Parkinson's diseases, inflammatory diseases, and the like.

The formulation described in the present invention may be administered once or a few times a day in an amount of about 10 to 2000 mg/day in terms of dry weight.

The active ingredients of the formulation according to the present invention can be added to various foods for the reduction of the serum lipid level or the total blood cholesterol level or accumulation of fat in tissues. Examples of foods to which the active ingredients according to the present invention can be added include tea beverages, juice, coffee, drinks, carbonated beverages, chewing gum, candies, caramels, chocolates and ice creams.

In additional aspects the protein or the composition comprising of protein as described in the present invention may be useful as veterinary medicine for the treatment and prophylaxis of diseases caused or aggravated by lipase and phospholipase activity in the body fluids, cells, and tissues in animals.

This invention further relates to a method for inhibiting or reducing lipase and phospholipase activity in body fluids, cells, and tissues by administration of a formulations comprising of the protein. The present invention is based on our discovery that the protein is a potent inhibitor of lipases and phospholipases using specific enzyme assays as disclosed herein later. Further, the invention is also based on our observation that the protein remains stable during formulation and thereby it would retain its activity.

The further aspects and features of the present invention are illustrated in the following non-limiting examples:

5. EXAMPLES

Example 1

Isolation of Lipase Inhibitory Protein from *Moringa* Seeds:

100 gm-powdered seeds were soaked in 1 litre MQ water for 48 hrs at room temperature. The extract was filtered through Whatman filter paper. The filtrate was concentrated using lyophlizer (−50° C.) for two days to get the protein isolate. Protein was estimated by using Bradford method.

Result: 10 mg powdered contained 494 µg protein.

Example 2

SDS-PAGE (17%) was performed with the protein isolated from *Moringa* seeds and stained with Coomassi blue. 5+/−1 kD band was cut and transferred to a siliconized tube and washed and destained in 200 µL 50% methanol overnight. The gel pieces were dehydrated in acetonitrile, rehydrated in 30 µL of 10 mM dithiolthreitol in 0.1 M ammonium bicarbonate and reduced at room temperature for 0.5 h. The DTT solution was removed and the sample alkylated in 30 μL 50 mM iodoacetamide in 0.1 M ammonium bicarbonate at room temperature for 0.5 h. The reagent was removed and the gel pieces dehydrated in 100 μL acetonitrile. The acetonitrile was removed and the gel pieces rehydrated in 100 μL 0.1 M ammonium bicarbonate. The pieces were dehydrated in 100 μL acetonitrile, the acetonitrile removed and the pieces completely dried by vacuum centrifugation. The gel pieces were rehydrated in 20 ng/μL trypsin in 50 mM ammonium bicarbonate on ice for 10 min. Any excess trypsin solution was removed and 20 μL 50 mM ammonium bicarbonate added. The sample was digested overnight at 37° C. and the peptides formed extracted from the polyacrylamide in two 30 μL aliquots of 50% acetonitrile/5% formic acid. These extracts were combined and evaporated to 25 μL for MS analysis.

The LC-MS system consisted of a Finnigan LCQ ion trap mass spectrometer system with a Protana nanospray ion source interfaced to a self-packed 8 cm×75 um id Phenomenex Jupiter 10 um C18 reversed-phase capillary column. 0.5-5 μL volumes of the extract were injected and the peptides eluted from the column by an acetonitrile/0.1 M acetic acid gradient at a flow rate of 0.25 μL/min. The nanospray ion source was operated at 2.8 kV. The digest was analyzed using the double play capability of the instrument acquiring full scan mass spectra to determine peptide molecular weights and product ion spectra to determine amino acid sequence in sequential scans.

The partial sequence ID of the protein was identified as shown below:

CGQQLRNISPPQRCPSLRQAVQLAHQQQGQGPQQVRQMYR

Example 3

Lipase Inhibitory Activity of *Moringa* Seed Protein in the Presence of Synthetic Substrate:

Lipase Assay:

Enzyme assay was performed by method described by Winkler and Stuckmann, 1979, with modification where there was use of pancreatic lipase. Assay was designed, using a 96-well format. The substrate used in this assay was p-nitrophenol palmitate (Sigma, Cat No—N-2752). 4.5 mg of p-nitrophenol palmitate was dissolved in 200 μl of N,N-dimethylformamide (Sigma, Cat No, D-4551) and volume made up to 10 ml with 0.1 M.Ph 8.0-phosphate buffer. Lipase (Sigma, Cat No, L-3126) sample was prepared by dissolving the enzyme in 0.1M-phosphate buffer at a concentration of 5 mg/ml. The reaction mixture consisted of substrate solution-150 μl; phosphate buffer (pH 8.0, 0.1 M)-40 μl and lipase solution-10 μl. The reaction mixture was incubated at 37° C. and optical density was measured at 405 nm after incubation. Enzyme activity was presented in the form of international unit (IU). One enzyme unit of lipase is defined as that quantity releasing 1 nm of free phenol from the substrate (p-nitro phenol palmitate)/ml/min under the standard assay condition (Winkler K. W. and Stuckman M, 1979 Glycogen hyaluronate and some other polysaccharides greatly enhances the formation of exolipase by *Serratia marcescens*, J. of Bacteriology 138: 663-670). It is derived from standard graph of p-nitro phenol.

Lipase Inhibition by *Moringa* Seed Protein

Inhibition assay was performed in a dose dependent manner The concentration of the protein checked 40 μg-0.156 μg/ml reaction mixture. The assay was similar to assay described above except 40 μl of inhibitor solution was used instead of phosphate buffer in control. Released p-nitro phenol was recorded at 405 nm. Enzyme inhibition was presented in the term of percentage inhibition simply on the basis of change in international unit (IU), which was calculated from standard graph.

Result:

TABLE 1

| Sample type | % Inhibition |
| --- | --- |
| Control (only enzyme) | 0.00 |
| Protein, 40 μg/ml | 100.00 |
| Protein, 20 μg/ml | 100.00 |
| Protein 10 μg/ml | 100.00 |
| Protein 5.0 μg/ml | 99.51 |
| Protein 2.5 μg/ml | 91.25 |
| Protein 1.25 μg/ml | 77.70 |
| Protein 0.625 μg/ml | 62.362 |
| Protein 0.312 μg/ml | 41.918 |
| Protein 0.156 μg/ml | 0.00 |

Conclusion: *Moringa* protein was able to inhibit the pancreatic lipase even at very low concentration.

Example 4

Inhibitory Activity of *Moringa* Seed Protein in the Presence of Natural Substrate:

Lipase activity was also measured by titrating free fatty acids liberated in the reaction mixture by following a modified method of "Ishiia C et al., 1988, Inhibition of lipase by proteins and their inhibitory mechanism, Nippon Shokuhin Kogyo Gakkaishi, 35 (6), 430-439. The reaction was performed in tubes by shaking at 37° C. for 30 min. the reaction mixture was prepared with 1.5 ml of McIlvaine buffer, pH-7.0, 0.24 ml of olive oil, and 0.5 ml of inhibitor solution and water all in final volume of 5.5 ml. After 5 min preincubation, the reaction was then started by adding 0.5 ml of enzyme solution (5.0 mg). The reaction was then stopped by the addition of 10 ml mixed solution of n-propyl alcohol: petroleum ether (1:4), and mixture was then shaken vigorously for 2 min 1 ml of upper layer was pippetted and titrated with 0.02 M alcoholic KOH using phenolphthalein as an indicator. The standard reaction mixture was prepared as described except that buffer substituted the inhibitor solution. Fatty acid released μM/min under standard assay condition was considered as one international unit (IU) of enzyme.

Result

TABLE 2

| Sample type | % Inhibition |
| --- | --- |
| Control 1, Heat killed enzyme | 0.00 |
| Control 2, Active enzyme | 00.00 |
| Enzyme + Protein (300 μg/ml) | 90.10 |
| Enzyme + Protein (150 μg/ml) | 90.10 |
| Enzyme + Protein (75.0 μg/ml) | 70.00 |
| Enzyme + Protein (37.5 μg/ml) | 50.00 |
| Enzyme + Protein (18.75 μg/ml) | 0.00 |

Conclusion: *Moringa* seed protein was able to inhibit the pancreatic lipase during the hydrolysis of natural substrate olive oil.

Example 5

Effect of Trypsin on Lipase Inhibitory Activity of *Moringa* Seed Protein:

The lipase inhibitory activity was performed after tryptic cleavage of *Moringa* seed protein. The isolated protein (500 μg/ml estimated by Bradford method) was incubated with trypsin (0.5%) in 50 mM, Tris buffer, pH-9.0 & sample buffer for 24 hrs at 37° C. in 1:1:2 ratio. After incubation all the samples were allowed for thermal inactivation at 70° C. for 10 min. The lipase inhibitory assay was performed as described earlier except 40 μl of test solution (trypsin treated/untreated) was used instead of phosphate buffer in control. Released p-nitro phenol was recorded at 405 nm. Lipase activity was presented in the term of percentage inhibition simply on the basis of change in international unit (IU), which was calculated from standard graph.

Result

TABLE 3

| Sample type | % Inhibition |
|---|---|
| Control, (only lipase) | 0.00 |
| Lipase + Protein | 100.00 |
| Lipase + Protein treated with trypsin | 18.17 |

Conclusion: *Moringa* seed protein lost the lipase inhibitory activity after tryptic cleavge which suggests the lipase inhibitory activity present of protein.

Example 6

Protection of *Moringa* Seed Protein from Trypsin with Soya Protein.

Isolation of Soya Protein from Soybean Seed

In a 2 litre glass beaker charge 500 gm soybean seed with 1.5 litre Milli Q water and heated the beaker in water bath at 65° C. (external temperature) for 90 min. after 90 min soya bean seed extract was filtered and cooled to room temperature. The filtrate was concentrated using lyophlizer (−50° C.) for two days. Crude protein stuck to the wall of round bottle flask and was scratched using spatula to fine powder. Total solid powder protein obtained was 12.5 gm with hygroscopic property. Protein was estimated by using Bradford method.

Result: 10 mg solid contained 18.52 μg protein

Protein Protection Assay

*Moringa* seed protein was protected against trypsin performed using various concentration of soya protein. The *Moringa* seed protein (49.1 μg/100 ul estimated by Bradford method) was incubated with 100 μl trypsin (0.5%) solution and various concentration 100 μl of soya protein in 50 mM, buffer, pH-9.0 & sample buffer for 24 hrs at 370° C. in 1:1:1:1 ratio. After incubation all the samples were allowed for thermal inactivation at 70° C. for 10 min. The assay was performed as described earlier except 40 μl of test solution (treated/untreated) was used instead of phosphate buffer in control. Released p-nitro phenol was recorded as OD at 405 nm. Lipase activity was presented in the term of percentage inhibition simply on the basis of change in international unit (IU), which was calculated from standard graph.

TABLE 4

| Sample type | % Inhibition |
|---|---|
| Control, (only lipase) | 0.00 |
| Lipase + Moringa seed protein | 100.00 |
| Lipase + Moringa seed protein treated with trypsin | 18.17 |
| Lipase + Moringa seed protein treated with trypsin + soya protein (1.852 ug) | 100.00 |
| Lipase + Moriga seed protein treated with trypsin + soya protein (0.926 ug) | 89.91 |
| Lipase + Moringa seed protein treated with trypsin + soya protein (0.463) | 32.08 |

Example 7

*Moringa* seed protein (50.0 gms), Microcrystalline Cellulose (336.0 gms) & Lactose (84.0 gms) were passed through 40# separately, & geometrical mixed in a suitable mixer for 15 minutes. 10% starch paste was prepared using Maize starch (30.0 gms) & required amount of water. Starch Paste was added in the mixer & mixing was continued until dough was formed with a consistency suitable for extrusion. The dough mixture was charged into a Fuji Paudal EXDS—60 extruder fitted with a 0.8 mm radial screen. The extrude were dried using drying oven at 40° C. for 8 hrs. Spheronise using Fuji Paudal Q230, dry these at 40° C. over night. The dried spherules were sifted through sieves, the spherules passed through 24 no. & retained over mesh n0. 40 for further processing.

Coating was done in two steps viz 1) Seal coating 2) Enteric coating.

Seal coating was done by using HPMC as a film forming polymer & enteric coating was done with the help of Eudragit L 30 D 55 as an enteric polymer & Yellow iron oxide as coloring agent.

The spherules were filled in size 0 hard gelatin transparent capsules.

The in-vitro protein analysis was done on Coated Spherules as well as on Filled capsules by using Brad ford Method.

Analytical Data:

TABLE 5

| Sr. No | Std/Sample | Blank OD (A) | Absorbance at 570 nm (B) | Absorbance (B − A) | Conc. ug/ml |
|---|---|---|---|---|---|
| 1. | 2 ul | 0.2525 | 0.369 | 0.1165 | 0.055 |
| 2. | 3.5 ul | 0.2525 | 0.488 | 0.2355 | .0096 |
| 3. | 7.0 ul | 0.2525 | 0.603 | 0.3505 | .0192 |
| 4. | 14.5 ul | 0.2525 | 0.746 | 0.4935 | 0.397 |
| 5. | 18.0 ul | 0.2525 | 0.876 | 0.6145 | 0.493 |
| 6. | Sample A* | 0.2525 | 0.774 | 0.5215 | A |
| 7. | Sample B** | 0.2525 | 0.7375 | 0.4850 | B |

Sample A* = Spherules sample
Sample B** = Filled Capsules sample

Graph was Plotted Conc. v/s Absorbance $R=0.950458$

Equation obtained: $Y=1.13616*X+0.0682681$,

Where Y is absorbance & X is concentration in ug/ul

From Calculation

Sample A*=0.3990 ug/ul

Sample B**=0.3668 ug/ul

From the above data it can be inferred that the protein does not get destroyed during the formulation process.

Example 8

Animal Study.

Short term animal experiment was performed with *Moringa* seed protein along with or without Soya protein (isolated earlier) in Wistar male rat in four groups. Male Wistar administered orally to the rat was deprived of food overnight, 1.2 ml of lipid emulsion (10 ml sunflower oil in water) or lipid emulsion 1.2 ml with various formulation in define groups (Group: control, Gruop-1: 50 mg soya seed extract solid (2.5 mg protein), Goup-2: Soya 50 mg solid extract contained 92.6 µg protein & Group-3: 50 mg *Moringa* solid extract (2.5 mg protein) & 50 mg soya solid extract (92.6 µg protein). Blood sample was taken and the plasma triacylglycerol concentration was determined.

Triglyceride Concentration (mg/dl)

Mean value:

|  | 0 hr | 1 hr | 2 hr | 3 hr |
| --- | --- | --- | --- | --- |
| Control | 69.16667 | 70.16667 | 76.16667 | 105.5 |
| Group 1 | 72.33333 | 70.16667 | 99.83333 | 115.5 |
| Group 2 | 102 | 57.83333 | 82.83333 | 99 |
| Group 3 | 77 | 59.33333 | 79.66667 | 84.83333 |

What is claimed is:

1. A protein comprising SEQ. IS. NO. 1:

CGQQLRNISPPQRCPSLRQAVQLAHQQQGQGPQQVRQMYR wherein the protein comprises between 40 amino acid residues up to 100 amino acid residues in length for use in a method of treating disorders associated with elevated lipase levels; and wherein the protein is produced by using any suitable method of protein isolation from plant material, or method of synthesis, or through recombinant DNA technology.

* * * * *

SEQUENCE LISTING

<160> NUMBER OF SEQ ID NOS: 1

<210> SEQ ID NO 1
<211> LENGTH: 40
<212> TYPE: PRT
<213> ORGANISM: Moringa

<400> SEQUENCE: 1

```
Cys Gly Gln Gln Leu Arg Asn Ile Ser Pro Pro Gln Arg Cys Pro Ser
1               5                   10                  15

Leu Arg Gln Ala Val Gln Leu Ala His Gln Gln Gln Gly Gln Gly Pro
            20                  25                  30

Gln Gln Val Arg Gln Met Tyr Arg
        35                  40
```